(12) United States Patent
Kipp et al.

(10) Patent No.: US 7,112,340 B2
(45) Date of Patent: Sep. 26, 2006

(54) COMPOSITIONS OF AND METHOD FOR PREPARING STABLE PARTICLES IN A FROZEN AQUEOUS MATRIX

(75) Inventors: James E. Kipp, Wauconda, IL (US); Mark J. Doty, Grayslake, IL (US); Christine L. Rebbeck, Algonquin, IL (US); Sean Brynjelsen, Lake in the Hills, IL (US); Jamie Teresa Konkel, Lakemoor, IL (US)

(73) Assignee: Baxter International Inc., Deerfield, IL (US)

( * ) Notice: Subject to any disclaimer, the term of this patent is extended or adjusted under 35 U.S.C. 154(b) by 131 days.

(21) Appl. No.: 10/270,267

(22) Filed: Oct. 11, 2002

(65) Prior Publication Data

US 2003/0077329 A1    Apr. 24, 2003

Related U.S. Application Data

(60) Provisional application No. 60/347,548, filed on Oct. 19, 2001.

(51) Int. Cl.
*A61K 9/14*  (2006.01)

(52) U.S. Cl. .................. 424/489; 424/484; 424/488

(58) Field of Classification Search ............ 424/489, 424/484, 488
See application file for complete search history.

(56) References Cited

U.S. PATENT DOCUMENTS

| | | | |
|---|---|---|---|
| 2,745,785 A | 1/1956 | Bruce et al. ............... 514/192 |
| 4,056,635 A | 11/1977 | Glen et al. ................ 424/346 |
| 4,073,943 A | 2/1978 | Wretlind et al. ........... 514/772 |
| 4,452,817 A | 6/1984 | Glen et al. ................ 424/346 |
| 4,540,602 A | 9/1985 | Motoyama et al. ...... 427/213.31 |
| 4,606,940 A | 8/1986 | Frank et al. |
| 4,608,278 A | 8/1986 | Frank et al. ............ 427/213.35 |
| 4,622,219 A | 11/1986 | Haynes ....................... 424/38 |
| 4,725,442 A | 2/1988 | Haynes ....................... 424/490 |
| 4,798,846 A | 1/1989 | Glen et al. ................ 514/713 |
| 4,826,689 A | 5/1989 | Violanto ..................... 424/489 |
| 4,973,465 A | 11/1990 | Baurain et al. ............. 424/406 |
| 4,997,454 A | 3/1991 | Violante et al. ........... 23/305 A |
| 5,023,271 A | 6/1991 | Vigne et al. ............... 514/458 |
| 5,049,322 A | 9/1991 | Devissaguet et al. |
| 5,078,994 A | 1/1992 | Nair et al. ................. 424/501 |
| 5,091,187 A | 2/1992 | Haynes ....................... 424/450 |
| 5,091,188 A | 2/1992 | Haynes ....................... 424/450 |
| 5,100,591 A | 3/1992 | Laclef et al. ................ 264/4.6 |
| 5,118,528 A | 6/1992 | Fessi et al. ............. 427/213.36 |
| 5,122,543 A | 6/1992 | Khanna |
| 5,133,908 A | 7/1992 | Stainmesse et al. ......... 264/4.1 |
| 5,145,684 A | 9/1992 | Liversidge et al. ......... 424/489 |
| 5,151,264 A | 9/1992 | Samain et al. |
| 5,152,923 A | 10/1992 | Weder et al. ................ 252/312 |
| 5,174,930 A | 12/1992 | Stainmesse et al. |
| 5,188,837 A | 2/1993 | Domb ....................... 424/450 |
| 5,246,707 A | 9/1993 | Haynes ...................... 424/450 |
| 5,250,236 A | 10/1993 | Gasco ......................... 264/4.4 |
| 5,269,979 A | 12/1993 | Fountain |
| 5,298,262 A | 3/1994 | Na et al. ..................... 424/489 |
| 5,302,401 A | 4/1994 | Liversidge et al. ......... 424/501 |
| 5,314,506 A | 5/1994 | Midler, Jr. et al. |
| 5,318,767 A | 6/1994 | Liversidge |
| 5,326,552 A | 7/1994 | Na et al. ...................... 424/4 |
| 5,336,507 A | 8/1994 | Na et al. ..................... 424/489 |
| 5,340,564 A | 8/1994 | Illig et al. .................... 424/9 |
| 5,346,702 A | 9/1994 | Na et al. ..................... 424/490 |
| 5,352,459 A | 10/1994 | Hollister et al. ............ 424/489 |
| 5,354,563 A | 10/1994 | Toyotama |
| 5,389,263 A | 2/1995 | Gallagher et al. .......... 210/729 |
| 5,399,363 A | 3/1995 | Liversidge et al. ......... 424/490 |
| 5,417,956 A | 5/1995 | Moser |
| 5,429,824 A | 7/1995 | June ........................... 424/489 |
| 5,447,710 A | 9/1995 | Na et al. ................... 424/9.455 |
| 5,466,646 A | 11/1995 | Moser |
| 5,470,583 A | 11/1995 | Na et al. ..................... 424/489 |
| 5,474,989 A | 12/1995 | Hashimoto et al. |
| 5,494,683 A | 2/1996 | Liversidge et al. ......... 424/490 |
| 5,510,118 A | 4/1996 | Bosch et al. ................ 424/489 |
| 5,518,187 A | 5/1996 | Bruno et al. |
| 5,518,738 A | 5/1996 | Eickhoff et al. ............. 424/493 |
| 5,534,270 A | 7/1996 | De Castro .................. 424/490 |
| 5,543,133 A | 8/1996 | Swanson et al. ........... 424/9.45 |

(Continued)

FOREIGN PATENT DOCUMENTS

EP    0379 379 B1    1/1990

(Continued)

OTHER PUBLICATIONS

B. Sjostrom et al., "The Formation of Submicron Organic Particles by Precipitation in an Emulsion", J.Dispersion Science and Technology, 15(1), 89-117 (1994).

(Continued)

*Primary Examiner*—Vickie Kim
*Assistant Examiner*—Thurman K. Page
(74) *Attorney, Agent, or Firm*—Michael C. Mayo; Raymond M. Mehler

(57) ABSTRACT

The present invention discloses a composition of a stable suspension of a poorly water soluble pharmaceutical agent or cosmetic in the form of particles of the pharmaceutical agent or cosmetic suspended in a frozen aqueous matrix and method for its preparation. The composition is stable for a prolonged period of time, preferably six months or longer and is suitable for parenteral, oral, or non-oral routes such as pulmonary (inhalation), ophthalmic, or topical administration.

91 Claims, No Drawings

U.S. PATENT DOCUMENTS

| | | |
|---|---|---|
| RE35,338 E | 9/1996 | Haynes |
| 5,552,160 A | 9/1996 | Liversidge et al. .......... 424/489 |
| 5,560,932 A | 10/1996 | Bagchi et al. ............... 424/489 |
| 5,560,933 A | 10/1996 | Soon-Shiong et al. ...... 424/489 |
| 5,565,383 A | 10/1996 | Sakai .......................... 437/200 |
| 5,569,448 A | 10/1996 | Wong et al. ................ 424/9.45 |
| 5,573,783 A | 11/1996 | Desieno et al. ............. 424/490 |
| 5,578,325 A | 11/1996 | Domb et al. ................ 424/501 |
| 5,580,579 A | 12/1996 | Ruddy et al. ............... 424/489 |
| 5,587,143 A | 12/1996 | Wong .......................... 424/9.1 |
| 5,591,456 A | 1/1997 | Franson et al. |
| 5,605,785 A | 2/1997 | Texter et al. ................ 430/546 |
| 5,626,864 A | 5/1997 | Rosenberg et al. |
| 5,635,609 A | 6/1997 | Levy et al. |
| 5,641,515 A | 6/1997 | Ramtoola ..................... 424/189 |
| 5,641,745 A | 6/1997 | Ramtoola |
| 5,660,858 A | 8/1997 | Parikh et al. ................ 424/450 |
| 5,662,883 A | 9/1997 | Bagchi et al. ................. 424/9.4 |
| 5,662,932 A | 9/1997 | Anselem et al. ............. 424/450 |
| 5,665,331 A | 9/1997 | Bagchi et al. .............. 424/9.45 |
| 5,665,383 A | 9/1997 | Grinstaff et al. ............. 424/450 |
| 5,707,634 A | 1/1998 | Schmitt |
| 5,716,642 A | 2/1998 | Bagchi et al. ............... 424/489 |
| 5,720,551 A | 2/1998 | Shechter ...................... 366/147 |
| 5,766,635 A | 6/1998 | Spenleuhauer et al. ..... 424/489 |
| 5,780,062 A | 7/1998 | Frank et al. ................. 424/501 |
| 5,833,891 A | 11/1998 | Subramaniam et al. ......... 264/7 |
| 5,858,410 A | 1/1999 | Muller et al. ................ 424/489 |
| 5,862,999 A | 1/1999 | Czekai et al. |
| 5,874,111 A | 2/1999 | Maitra et al. ................ 424/499 |
| 5,916,583 A | 6/1999 | Broberg et al. |
| 5,916,596 A | 6/1999 | Desai et al. ................. 424/489 |
| 5,922,355 A | 7/1999 | Parikh et al. ................ 424/489 |
| 5,939,100 A | 8/1999 | Albrechtsen et al. |
| 5,981,719 A | 11/1999 | Woiszwillo et al. ......... 530/410 |
| 5,989,583 A | 11/1999 | Amselem |
| 6,007,845 A | 12/1999 | Domb et al. ................. 424/501 |
| 6,039,981 A | 3/2000 | Woo et al. |
| 6,045,826 A | 4/2000 | Borowy-Borowski et al. |
| 6,045,829 A | 4/2000 | Liversidge et al. .......... 424/489 |
| 6,048,550 A | 4/2000 | Chan et al. .................. 424/497 |
| 6,063,910 A | 5/2000 | Debenedetti et al. ........ 530/418 |
| 6,068,858 A | 5/2000 | Liversidge et al. .......... 424/489 |
| 6,086,376 A | 7/2000 | Moussa et al. ................. 434/45 |
| 6,090,925 A | 7/2000 | Woiszwillo et al. ......... 530/410 |
| 6,090,983 A | 7/2000 | Yokoyama et al. .......... 564/346 |
| 6,132,750 A | 10/2000 | Perrier et al. ................ 424/418 |
| 6,139,870 A | 10/2000 | Verrecchia |
| 6,143,211 A | 11/2000 | Mathiowitz et al. ............ 264/4 |
| 6,146,663 A | 11/2000 | Bissery et al. ............... 424/489 |
| 6,153,225 A | 11/2000 | Lee et al. ..................... 424/501 |
| 6,165,506 A | 12/2000 | Jain et al. ..................... 424/466 |
| 6,177,103 B1 | 1/2001 | Pace et al. ................... 424/489 |
| 6,197,757 B1 | 3/2001 | Perrier et al. ................... 514/53 |
| 6,207,134 B1 | 3/2001 | Fahlvik et al. |
| 6,214,384 B1 | 4/2001 | Pallado et al. ............... 424/493 |
| 6,217,886 B1 | 4/2001 | Onyuksel et al. ............ 424/401 |
| 6,221,322 B1 | 4/2001 | Thumm et al. |
| 6,221,398 B1 | 4/2001 | Jakupovic et al. |
| 6,221,400 B1 | 4/2001 | Liversidge et al. .......... 424/489 |
| 6,228,399 B1 | 5/2001 | Parikh et al. ................ 424/489 |
| 6,231,890 B1 | 5/2001 | Naito et al. |
| 6,235,224 B1 | 5/2001 | Mathiowitz ..................... 264/4 |
| 6,238,677 B1 | 5/2001 | Fanta et al. .................. 424/400 |
| 6,238,694 B1 | 5/2001 | Gasco ........................... 424/450 |
| 6,245,349 B1 | 6/2001 | Yiv et al. ..................... 424/450 |
| 6,248,363 B1 | 6/2001 | Patel et al. ................... 424/497 |
| 6,264,922 B1 | 7/2001 | Wood et al. .................... 424/45 |
| 6,267,989 B1 | 7/2001 | Liversidge ................... 424/489 |
| 6,268,053 B1 | 7/2001 | Woiszwillo et al. ......... 428/402 |
| 6,270,806 B1 | 8/2001 | Liversidge et al. .......... 424/497 |
| 6,294,204 B1 | 9/2001 | Rossling et al. ............. 424/497 |
| 6,299,906 B1 | 10/2001 | Bausch et al. ............... 424/489 |
| 6,306,406 B1 | 10/2001 | Deluca |
| 6,337,092 B1 | 1/2002 | Khan et al. .................. 424/489 |
| 6,344,271 B1 | 2/2002 | Yadav et al. |
| 6,346,533 B1 | 2/2002 | Cha et al. ............... 514/245.05 |
| 6,365,191 B1 | 4/2002 | Burman et al. |
| 6,375,986 B1 | 4/2002 | Ryde et al. |
| 6,395,300 B1 * | 5/2002 | Straub et al. ................ 424/489 |
| 6,428,814 B1 | 8/2002 | Bosch et al. |
| 6,462,093 B1 | 10/2002 | Miyamoto et al. |
| 6,607,784 B1 | 8/2003 | Kipp et al. |
| 2001/0007678 A1 | 7/2001 | Baert et al. |
| 2001/0025058 A1 | 9/2001 | Borowy-Borowski et al. |
| 2001/0042932 A1 | 11/2001 | Mathiowtiz et al. |
| 2002/0012675 A1 | 1/2002 | Jain et al. |
| 2002/0012704 A1 | 1/2002 | Pace et al. |
| 2002/0041896 A1 | 4/2002 | Straub et al. |
| 2002/0054912 A1 | 5/2002 | Kim et al. |
| 2002/0110599 A1 | 8/2002 | Auweter et al. |
| 2002/0127278 A1 | 9/2002 | Kipp et al. |
| 2002/0168402 A1 | 11/2002 | Kipp et al. |
| 2003/0003155 A1 | 1/2003 | Kipp et al. |
| 2003/0031719 A1 | 2/2003 | Kipp et al. |
| 2003/0044433 A1 | 3/2003 | Werling et al. |
| 2003/0054042 A1 | 3/2003 | Liversidge et al. |
| 2003/0059472 A1 | 3/2003 | Brynjelsen et al. |
| 2003/0072807 A1 | 4/2003 | Wong et al. |
| 2003/0096013 A1 | 5/2003 | Werling et al. |
| 2003/0100568 A1 | 5/2003 | Werling et al. |
| 2003/0206959 A9 | 11/2003 | Kipp et al. |

FOREIGN PATENT DOCUMENTS

| | | |
|---|---|---|
| EP | 0498482 B1 | 8/1992 |
| EP | 0499299 B1 | 8/1992 |
| EP | 0517565 B1 | 12/1992 |
| EP | 0349 428 B1 | 1/1993 |
| EP | 0377 477 B1 | 3/1993 |
| EP | 0535534 A1 | 4/1993 |
| EP | 0169 618 B2 | 11/1993 |
| EP | 0577215 A1 | 5/1994 |
| EP | 0600532 A2 | 6/1994 |
| EP | 0600532 A3 | 6/1994 |
| EP | 0601618 A2 | 6/1994 |
| EP | 0601618 A3 | 6/1994 |
| EP | 0601619 A2 | 6/1994 |
| EP | 0601619 A3 | 6/1994 |
| EP | 0602700 A2 | 6/1994 |
| EP | 0602700 A3 | 6/1994 |
| EP | 0602702 A1 | 6/1994 |
| EP | 0605024 A2 | 7/1994 |
| EP | 0605024 A3 | 7/1994 |
| EP | 0207 134 B1 | 8/1994 |
| EP | 0275 796 B2 | 9/1995 |
| EP | 0820 300 B1 | 4/1996 |
| EP | 0372 070 B1 | 1/1997 |
| EP | 0754034 B1 | 1/1997 |
| EP | 0644 755 A1 | 3/1997 |
| EP | 0832 569 A2 | 4/1998 |
| EP | 0730 406 B1 | 7/1998 |
| EP | 0498482 B1 | 9/1999 |
| EP | 0831 770 B1 | 8/2000 |
| EP | 0988 863 A3 | 8/2000 |
| EP | 0499299 B1 | 8/2000 |
| EP | 0517565 B1 | 10/2000 |
| EP | 0808154 B1 | 12/2000 |
| EP | 0720 471 B1 | 4/2001 |
| EP | 0804162 B1 | 9/2001 |
| EP | 0828 479 B1 | 10/2001 |
| EP | 0788 350 B1 | 2/2002 |
| EP | 0752 245 B1 | 5/2002 |
| EP | 1210 942 A2 | 6/2002 |

| | | | |
|---|---|---|---|
| EP | 1012 204 B1 | 1/2003 |
| EP | 1156 788 A1 | 1/2003 |
| EP | 1105 109 B1 | 4/2003 |
| EP | 0812 187 A1 | 5/2003 |
| EP | 0832 569 B1 | 11/2003 |
| WO | WO 85/00011 A1 | 1/1985 |
| WO | WO 86/03676 A1 | 7/1986 |
| WO | WO 89/11850 A1 | 12/1989 |
| WO | WO 90/03782 A2 | 4/1990 |
| WO | WO 90/15593 A1 | 12/1990 |
| WO | WO 91/06292 A1 | 5/1991 |
| WO | WO 91/12794 A1 | 9/1991 |
| WO | WO 91/16068 A1 | 10/1991 |
| WO | WO 92/00731 A1 | 1/1992 |
| WO | WO 92/03380 A1 | 3/1992 |
| WO | WO 93/25190 A1 | 12/1993 |
| WO | WO 94/20072 A1 | 9/1994 |
| WO | WO 95/05164 A1 | 2/1995 |
| WO | WO 95/27482 A1 | 10/1995 |
| WO | WO 95/33488 A1 | 12/1995 |
| WO | WO 96/00567 A1 | 1/1996 |
| WO | WO 96/14833 A1 | 5/1996 |
| WO | WO 96/20698 A2 | 7/1996 |
| WO | WO 97/03657 A1 | 7/1996 |
| WO | WO 96/24336 A1 | 8/1996 |
| WO | WO 96/24340 A1 | 8/1996 |
| WO | WO 96/25150 A1 | 8/1996 |
| WO | WO 96/25152 A1 | 8/1996 |
| WO | WO 96/25918 A1 | 8/1996 |
| WO | WO 96/31231 A1 | 10/1996 |
| WO | WO 97/03651 | * | 2/1997 |
| WO | WO 97/14407 A1 | 4/1997 |
| WO | WO 97/30695 A1 | 8/1997 |
| WO | WO 97/36611 A1 | 10/1997 |
| WO | WO 97/41837 A2 | 11/1997 |
| WO | WO 97/44014 A1 | 11/1997 |
| WO | WO 98/07410 A1 | 2/1998 |
| WO | WO 98/07414 A1 | 2/1998 |
| WO | WO 98/14174 | * | 4/1998 |
| WO | WO 98/14174 A1 | 4/1998 |
| WO | WO 98/14180 A1 | 4/1998 |
| WO | WO 98/24450 A1 | 6/1998 |
| WO | WO 98/35666 A1 | 8/1998 |
| WO | WO 98/57967 A1 | 12/1998 |
| WO | WO 99/00113 A1 | 1/1999 |
| WO | WO 99/02665 A1 | 1/1999 |
| WO | WO 99/03450 A1 | 1/1999 |
| WO | WO 99/16443 A1 | 4/1999 |
| WO | WO 99/29316 A1 | 6/1999 |
| WO | WO 99/30833 A1 | 6/1999 |
| WO | WO 99/32156 A2 | 7/1999 |
| WO | WO 99/33467 A1 | 7/1999 |
| WO | WO 99/38493 A1 | 8/1999 |
| WO | WO 99/49846 A2 | 10/1999 |
| WO | WO 99/49848 A1 | 10/1999 |
| WO | WO 99/61001 A1 | 12/1999 |
| WO | WO 99/65469 A3 | 12/1999 |
| WO | WO 00/06152 | * | 2/2000 |
| WO | WO 00/09096 B1 | 2/2000 |
| WO | WO 00/12124 A1 | 3/2000 |
| WO | WO 00/12125 A1 | 3/2000 |
| WO | WO 00/18374 A1 | 4/2000 |
| WO | WO 00/27363 A1 | 5/2000 |
| WO | WO 00/30615 A1 | 6/2000 |
| WO | WO 00/30616 A1 | 6/2000 |
| WO | WO 00/37050 A1 | 6/2000 |
| WO | WO 00/40220 A1 | 7/2000 |
| WO | WO 00/51572 B1 | 9/2000 |
| WO | WO 00/71079 A2 | 11/2000 |
| WO | WO 01/12155 A1 | 2/2001 |
| WO | WO 01/17546 A1 | 3/2001 |
| WO | WO 01/26635 A2 | 4/2001 |
| WO | WO 01/62374 A2 | 8/2001 |
| WO | WO 01/64164 A2 | 9/2001 |
| WO | WO 01/80828 A2 | 11/2001 |
| WO | WO 01/85345 A1 | 11/2001 |
| WO | WO 01/87264 A2 | 11/2001 |
| WO | WO 02/17883 A2 | 3/2002 |
| WO | WO 02/24163 A1 | 3/2002 |
| WO | WO 02/24169 A1 | 3/2002 |
| WO | WO 02/43702 A2 | 6/2002 |
| WO | WO 02/51386 A2 | 7/2002 |
| WO | WO 02/055059 A2 | 7/2002 |
| WO | WO 02/55059 A2 | 7/2002 |
| WO | WO 02/60411 A2 | 8/2002 |
| WO | WO 02/72070 A1 | 9/2002 |
| WO | WO 02/72071 A1 | 9/2002 |
| WO | WO 02/74282 A1 | 9/2002 |
| WO | WO 02/80883 A2 | 10/2002 |
| WO | WO 02/89773 A2 | 11/2002 |
| WO | WO 03/024424 A1 | 3/2003 |
| WO | WO 03/26611 A2 | 4/2003 |
| WO | WO 03/26611 A3 | 4/2003 |
| WO | WO 03/35031 A1 | 5/2003 |

OTHER PUBLICATIONS

Avanti Polar Lipids, Inc.., website printout, www.avantilipids.com, "Synthetic Products—Functionalized Phospholipids: Lipids for Conjugation of Proteins/Peptides/Drugs to Liposomes" (7 pgs), Mar. 2003.

Avanti Polar Lipids, Inc.., website printout, www.avantilipids.com, "Polymer and Polymerizable Lipids: Functionalized PEG Lipids" (3 pgs), Mar. 2003.

Avanti Polar Lipids, Inc.., website printout, www.avantilipids.com, "Polymer and Polymerizable Lipids: Poly(ethylene glycol)-Lipid Conjugates" (8 pgs), Mar. 2003.

Davis et al., "Pulmonary Perfusion Imaging: Acute Toxicity and Safety Factors as a Function of Particle Size", *J.Nucl Med.*, vol. 19 (1978), pp. 1209-1213.

Schroeder et al., "Physiological Effects of Subvisible Microspheres Administered Intravenously to Beagle Dogs", *Journal of Pharmaceutical Sciences*, vol. 67, No. 4, Apr. 1978, pp. 508-512.

Yokel et al., "Acute Toxicity of Latex Microspheres", *Toxicity Letters*, vol. 9 (1981), pp. 165-170.

Allen et al., "Critical Evaluation of Acute Cardiopulminary Toxicity of Microspheres", *J.Nucl Med.*, vol. 19 (1987), pp. 1204-1208.

B. Sjostrom et al., "Preparation Of Submicron Drug Particles In Lecithin-Stabilized O/W Emulsions I. Model Studies Of The Precipitation Of Cholesteryl Acetate", *Int. J. Pharm.*, 88 (1992) pp. 53-62.

B. Sjostrom et al., "A Method For The Preparation Of Submicron Particles Of Sparingly Water-Soluble Drugs By Precipitation In Oil-In-Water Emulsions. II: Influence Of The Emulsifier, The Solvent And The Drug Substance" , *J. Pharm. Sci.*, 82(6), (1992) pp. 584-589.

Duncker and Reichelt, "Effects of the Pharmaceutical Cosolvent hydroxypropyl-beta-cyclodextrin on Porcine Corneal Endothelium", *Graefe's Archive for Clinical and Experimental Ophthalmology* (Germany), 236/5 (1998), pp. 380-389.

Volchek and Dellen, "Anaphylaxis to Intravenous Cyclosporine and Tolerance to Oral Cyclosporine, Case Report and Review", *Annals of Allergy, Asthma, and Immunology*, 80 (1998), pp. 159-163.

Singla et al., "Paclitaxel and its Formulations", *International Journal of Pharmaceutics*, 235/1-2 (2002), pp. 179-192.

Publication: "The Effects of Freezing on Commercial Insulin Suspensions", by D.T. Graham and A.R. Pomeroy, published by International Journal of Pharmaceutics, 1978.

PCT/US2002/33270 International Search Report, dated Jan. 31, 2003.

US 5,849,884, 12/1998, Woiszwillo et al. (withdrawn)

* cited by examiner

COMPOSITIONS OF AND METHOD FOR PREPARING STABLE PARTICLES IN A FROZEN AQUEOUS MATRIX

CROSS-REFERENCE TO RELATED APPLICATIONS

This application claims priority from provisional Application Ser. No. 60/347,548 filed Oct. 19, 2001, which is incorporated herein by reference and made a part hereof.

FEDERALLY SPONSORED RESEARCH OR DEVELOPMENT

Not Applicable.

BACKGROUND OF THE INVENTION

1. Technical Field

The present invention discloses a composition of a stable suspension of a poorly water soluble compound comprising particles of the compound suspended in a frozen aqueous matrix and method for its preparation. The composition is stable for a prolonged period of time, preferably six months or longer.

2. Background Art

There is an ever increasing number of pharmaceutical compounds being formulated that are poorly soluble or insoluble in aqueous solutions. Such compounds provide challenges to delivering them in an injectable form. Drugs that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981). One solution to this problem is the production of extremely small particles of the insoluble drug candidate and the creation of a microparticulate or nanoparticulate suspension. In this way, drugs that were previously unable to be formulated in an aqueous based system can be made suitable for intravenous administration. Suitability for intravenous administration includes small particle size (<7 μm), low toxicity (as from toxic formulation components or residual solvents), and bioavailability of the drug particles after administration.

Suspensions may also be suitable for oral, intramucscular, pulmonary, topical or subcutaneous administration. When administered by these routes, it may be desirable to have particle size in the range of 5 to 100 microns.

Suspensions may lack sufficient physical and chemical stability when stored for a prolonged period of time. Physical instability occurs when the particles aggregate to form larger particles, which is generally the result of small particle size. Ostwald-Mie ripening may occur due to the small particle radius and attendant increase in surface activity, hence solubility. In particular, nanoparticles have a very high surface-to-volume ratio which enhances their dissolution rate and solubility. As a result, the particles may solubilize in the suspension followed by recrystallization to form large crystals. Aggregation and crystal growth result in suspensions of nanoparticles with larger and varying particle sizes. Suspensions with particles larger than 7 μm are no longer suitable for intravenous administration.

In a suspension, the active ingredient may also undergo degradation and result in reduced activity over time due to interaction with the suspension medium. Even slight dissolution may accelerate the degradation of the active ingredient. The rate of chemical degradation depends on particle size, intrinsic solubility, and the chemical nature of the active ingredient.

It is highly desirable to have a pharmaceutical preparation of an aqueous suspension with a long shelf life, preferably a minimum of six months in terms of both physical and chemical stabilities.

Several methods have been described in the prior art to limit aggregation and crystal growth of nanoparticles in suspension to improve their physical stability and shelf-life. One method includes the step of adding surface stabilizers to the preparations. Suitable surface stabilizers include surfactants, polymers, cloud point modifiers (see U.S. Pat. Nos. 5,298,262; 5,346,702; and 5,470,583), crystal growth modifiers (see U.S. Pat. No. 5,665,331), and cryoprotectants (see U.S. Pat. No. 5,302,401). While such approaches have found success in limiting-particle aggregation and crystal growth, suitable surface-active agents may not be found that would enable extended storage of the suspension in the liquid state, either at room temperature or in the refrigerator. Or, if stabilizing agents could be found, they may possess undesirable toxicity profiles.

Another approach to inhibiting the aggregation and crystal growth of nanoparticles is to limit the average particle size to a narrow range of from about 150 nm to about 350 nm, as described by Liversidge et al. in U.S. Pat. No. 6,267,989. The '989 patent discloses that aggregation and crystal growth are minimized when the particles are within this size range. However, the narrow range of the particle sizes limits its applications. For certain applications, it may be desirable to have nanoparticle suspensions with particle sizes in excess of 400 nm. These applications include, but are not limited to, oral, subcutaneous, or intramuscular administration in which the desirable particle size may be from 5 to 100 microns. In other formulations, the desirable particle size may be smaller than 100 nm. This is true, for example, for particles designed to evade the RES (reticuloendothelial system). Such long-circulating particles can also migrate across loose, fenestrated vasculature such as that associated with certain cancerous tumors. This would facilitate passive targeting of such tumors.

Yiv et al. discloses in U.S. Pat. No. 6,245,349 a stable formulation of lipid nanoparticles of lipophilic and amphipathic drugs. The formulation is an oil-in-water microemulsion consisting of phospholipid, propylene glycol, polyethylene glycol, a surfactant and water. An oil component such as a triglyceride is optional. The components are blended together to form an emulsion. The average particle size should be smaller than 200 nm-for the preparation to be filter sterilized. The composition can be stored either in a concentrated form or a diluted form. The diluted form includes an aqueous buffer and is stable at a temperature range of about −50° C. to about 40° C. In Example 1, the composition was stored at −20° C. for 21 days with no evidence of phase separation, change in particle size, or drug crystallization. The method, however, is limited to oil-in-water dispersions with particle sizes smaller than 200 nm, wherein all components are liquids. Such dispersions are commonly sterilized by filter sterilization which requires the dispersion be passed through filters with a pore size of 220 nm.

The prior art also describes methods of improving the chemical stability of nanoparticle preparations for prolonged storage. The general approach is to remove the aqueous medium by lyophilization and store the nanoparticles in dry, lyophilized form. An example is disclosed in Example 6 of U.S. Pat. No. 5,091,187. Dialysis is generally required before lyophilization to remove any unwanted solutes, such as salt, or to prevent the concentration of such solutes during the lyophilization process. The additional steps of dialysis and lyophilization increase production costs since dialysis is a very time consuming process and lyophilization is an energy consuming process. Furthermore, the lyophilized preparation requires reconstitution with an appropriate dispersing medium before administration either by injection (intravenously, intramuscularly, or subcutaneously), or orally. Such requires more labor in administering the pharmaceutical agent as well as introducing potential human errors that can occur during reconstitution.

As part of an effort to develop new methods for stabilization of these suspensions, we have discovered that freezing may circumvent these instability mechanisms by encasing the drug particles in a frozen aqueous matrix. At such low temperatures, drug solubility is reduced and very high viscosity of the aqueous medium disfavors diffusion of solute drug away from the solid particle. This includes nucleation, crystal growth and Ostwald ripening. Lower temperatures also increase chemical stability by slowing down drug degradation in the aqueous medium. Crystallization of water may also occur, for example below the eutectic point of the mixture, thus eliminating the possibility of forming a solution phase containing drug which can undergo secondary nucleation, crystal growth and Ostwald ripening.

The nanoparticles in the invention can be prepared from any of the known methods in the art. One approach centers on reducing the size of the particles that deliver the drug. In one such series of patents, which include U.S. Pat. Nos. 6,228,399; 6,086,376; 5,922,355; and 5,660,858, Parikh et al. discloses that sonication may be used to prepare microparticles of the water-insoluble compound. Of these patents, U.S. Pat. No. 5,922,355 discloses an improvement to a method that uses sonication for making smaller particles. The improvement comprises mixing an active pharmacological agent with a phospholipid and surfactants in a single-phase aqueous system and applying energy to the system to produce smaller particles. Stabilization of the suspension by freezing is not disclosed, however.

U.S. Pat. No. 5,091,188, issued to Haynes, also discloses reducing the size of particles of a pharmacologically active water-insoluble drug and employing a lipid coating on the particles to confer a solid form. The patent is directed to a pharmaceutical composition consisting essentially of an aqueous suspension of solid particles of the drug having a diameter of about 0.05 to about 10 microns. The lipid coating affixed to the surface of the particles acts to stabilize them. The composition is produced by adding the drug to water in the presence of membrane-forming lipid surfactants and then reducing the particle size within the aqueous suspension. However, freezing the suspension is not disclosed as a stabilization method.

U.S. Pat. No. 5,858,410 discloses a pharmaceutical nanosuspension suitable for parenteral administration. The '410 patent discloses subjecting at least one solid therapeutically active compound dispersed in a solvent to high pressure homogenization in a piston-gap homogenizer to form particles having an average diameter, determined by photon correlation spectroscopy (PCS) of 10 nm to 1000 nm, the proportion of particles larger than 5 microns in the total population being less than 0.1% (number distribution determined with a Coulter counter), without prior conversion into a melt, wherein the active compound is solid at room temperature and is insoluble, only sparingly soluble or moderately soluble in water, aqueous media and/or organic solvents. The Examples in the '410 patent disclose jet milling prior to homogenization.

U.S. Pat. No. 5,145,684 discloses another approach to providing nanoparticles of insoluble drugs for parenteral delivery by reducing the size of the particles. The '684 patent discloses the wet milling of an insoluble drug in the presence of a surface modifier to provide a drug particle having an average effective particle size of less than 400 nm. The '684 patent emphasizes the desirability of not using any solvents in its process. The '684 patent discloses the surface modifier is adsorbed on the surface of the drug particle in an amount sufficient to prevent agglomeration into larger particles.

Besides physically reducing the size of drug particles and coating the particles with a surface stabilizer, nanoparticles can also be prepared by the various methods of precipitation. These methods typically involve dissolving the drug in a solvent as a continuous phase followed by changing the conditions of the solution to a non-continuous phase so that fine particles of the drug precipitate out into the non-continuous phase. A coating agent or surface stabilizer is normally used to co-precipitate with the drug to stabilize the particles. Examples of these precipitation methods are solvent and anti-solvent microprecipitation, phase inversion precipitation, pH shift precipitation, supercritical fluid precipitation, and temperature shift precipitation.

Examples of appropriate precipitation techniques include preparing nanoparticle suspensions as disclosed in U.S. Patent Application Ser. Nos. 60/258,160; 09/874,799; 09/874,637; 09/874,499; and 09/953,979, which are incorporated herein by reference and made a part hereof. These applications disclose forming small particles of organic compounds by dissolving the organic compound in a water miscible organic solvent followed by precipitating the organic compounds in an aqueous medium to form a pre-suspension followed by adding energy to the pre-suspension to stabilize a coating of the particle, to alter the lattice structure of the particle or to reduce particle size. The process is preferably used to prepare a suspension of a poorly water-soluble, pharmaceutically active compound.

U.S. Pat. No. 5,118,528 discloses a process for preparing nanoparticles by solvent anti-solvent precipitation. The process includes the steps of: (1) preparing a liquid phase of a substance in a solvent or a mixture of solvents to which may be added one or more surfactants, (2) preparing a second liquid phase of a non-solvent or a mixture of non-solvents, the non-solvent is miscible with the solvent or mixture of solvents for the substance, (3) adding together the solutions of (1) and (2) with stirring; and (4) removing of unwanted solvents to produce a colloidal suspension of nanoparticles. The '528 patent discloses that it produces particles of the substance smaller than 500 nm without the supply of energy. In particular, the '528 patent states that it is undesirable to use high energy equipment such as sonicators and homogenizers.

U.S. Pat. No. 4,826,689 discloses a method for making uniformly sized particles from water-insoluble drugs or other organic compounds. First, a suitable solid organic compound is dissolved in an organic solvent, and the solution can be diluted with a non-solvent. Then, an aqueous precipitating liquid is infused, precipitating non-aggregated particles with substantially uniform mean diameter. The particles are then separated from the organic solvent. Depending on the organic compound and the desired particle size, the parameters of temperature, ratio of non-solvent to organic solvent, infusion rate, stir rate, and volume can be varied according to the invention. The '689 patent discloses this process forms a drug in a metastable state which is thermodynamically unstable. The '689 patent discloses trapping the drug in a metastable state by utilizing crystallization inhibitors (e.g., polyvinylpyrrolidinone) and surface-active agents (e.g., poly(oxyethylene)-co-(oxypropylene)) to render the metastable precipitate stable enough to be isolated by centrifugation, membrane filtration or reverse osmosis.

U.S. Pat. No. 5,780,062 discloses a method of preparing small particles of insoluble drugs by (1) dissolving the drug in a water-miscible first solvent, (2) preparing a second solution of a polymer and an amphiphile in an aqueous second solvent in which the drug is substantially insoluble whereby a polymer/amphiphile complex is formed and (3) mixing the solutions from the first and second steps to precipitate an aggregate of the drug and polymer/amphiphile complex.

U.S. Pat. No. 4,997,454 discloses a method for making uniformly sized particles from solid compounds. The method of the '454 patent includes the steps of dissolving the solid compound in a suitable solvent followed by infusing precipitating liquid thereby precipitating non-aggregated particles with substantially uniform mean diameter. The particles are then separated from the solvent. The '454 patent discourages forming particles in a crystalline state because during the precipitating procedure the crystal can dissolve and recrystallize thereby broadening the particle size distribution range. The '454 patent encourages during the precipitating procedure to trap the particles in a thermodynamically unstable particle state.

U.S. Pat. Nos. 6,235,224 B1 and 6,143,211, both issued to Mathiowitz et al., disclose the use of phase inversion phenomena to precipitate microencapsulated microparticles. The method includes mixing a polymer and a drug with a solvent. This mixture is introduced into an effective amount of a miscible non-solvent, thereby causing spontaneous formation of the microencapsulated product.

Microprecipitation by pH shifting is another technology used to prepare dispersions of a nanoparticulate pharmaceutical agent. See, e.g., U.S. Pat. Nos. 5,766,635; 5,716,642; 5,665,331; 5,662,883; 5,560,932; and 4,608,278. This technology involves dissolving a pharmaceutical compound in an aqueous base having a non-neutral pH that is then neutralized to precipitate the compound in the aqueous base.

In yet another approach, such as that disclosed in U.S. Pat. No. 5,766,635, issued to Spenlenhauer et al., nanoparticles have been prepared by dissolving a poly(ethylene) oxide and/or poly(propylene) oxide/polylactide copolymer in an organic solvent, mixing the organic solution so formed with an aqueous solution to cause nanoparticles to precipitate out of solution, and microfluidizing the suspension without the use of surfactants. Carrier particles consisting of a solid polymer matrix are thus formed, into which a co-precipitated pharmaceutical agent may be incorporated.

Precipitation by supercritical fluid is disclosed by U.S. Pat. Nos. 5,360,478 and 5,389,263 to Krukonis et al., and WO 97/14407 to Johnston. The technology is similar to the solvent anti-solvent precipitation method. In this case, the supercritical fluid, which can be a gas or liquid at conditions of pressure and temperature above its critical point, acts as the anti-solvent. The addition of the supercritical fluid to a solution of a solute in a solvent causes the solute to attain or approach supersaturated state and to precipitate out as fine particles.

Temperature shift precipitation is disclosed in U.S. Pat. No. 5,188,837 to Domb. The method involves adding a thermally stable drug to a polymer. The polymer is often oil-based (e.g., phospholipid, synthetic waxes) and has a low melting point. The drug is heated with the polymer to slightly above the melting point of the polymer to form a warm emulsion of the drug in the molten polymer. The emulsion is then cooled quickly by adding the emulsion to a bath of cold non-solvent, such as water, with vigorous shaking to cause the emulsion to form droplets and to solidify to entrap the active agent in a suspension.

Yet another approach to preparing submicron particles of poorly water soluble organic compounds is the formation of an emulsion of the compound. The organic compound is dissolved in an organic phase. The organic phase forms an emulsion with an aqueous phase. An emulsion evaporation method is disclosed in U.S. patent application Ser. No. 09/964,273. The method includes the steps of: (1) providing a multiphase system having an organic phase and an aqueous phase, the organic phase having a pharmaceutically effective compound therein; and (2) sonicating the system to evaporate a portion of the organic phase to cause precipitation of the compound in the aqueous phase and having an average effective particle size of less than about 400 nm.

U.S. Pat. No. 5,605,785 discloses a process for forming nanoamorphous dispersions of photographically useful compounds. The process of forming nanoamorphous dispersions include any known process of emulsification that produces a dispersed phase having amorphous particulates.

Still yet another approach to preparing submicron size nanoparticle suspension of a pharmaceutically active compound is by seeding at some point during a precipitation process to generate crystals of a desired morphology. (see U.S. patent application Ser. No. 10/035,821). The method comprises the steps of dissolving a first quantity of the pharmaceutically-active compound in the water-miscible first organic solvent to form a first solution. The first solution is then seeded. Alternatively, a second solvent may be seeded. It is also possible to use seed compounds at other points during the precipitation process. The first solution is then mixed with the second solvent. The mixing of the first solution with the second solvent results in the precipitation of the pharmaceutically-active compound in a desired morphological form.

Another approach is directed to the production of suspended particles coated with protein. U.S. Pat. No. 5,916,596, issued to Desai et al., discloses the application of high shear to a mixture of an organic phase having a pharmacologically active agent dispersed therein and an aqueous medium containing a biocompatible polymer. The mixture is sheared in a high-pressure homogenizer at a pressure in the range of from about 3,000 to 30,000 psi. The '596 patent requires the mixture contain substantially no surfactants because the combined use of a surfactant with a protein results in the formation of large, needle-like crystalline particles that increase in size during storage. See columns 17–18, example 4.

U.S. Pat. No. 5,560,933, issued to Soon-Shiong et al., discloses the formation of a polymeric shell around the water-insoluble drug for in vivo delivery. The method discloses the application of sonication to a mixture comprising a polymer-containing aqueous medium and a dispersing agent having a substantially water-insoluble drug dispersed therein. In this reference, sonication is used to drive the formation of disulfide bonds in the polymer, causing it to cross-link so as to produce a polymeric shell around the drug. Sonication is conducted for a time sufficient for the disulfide bonds to form.

In U.S. Pat. No. 5,665,383, Grinstaff et al. discloses the application of ultrasound to a single-phase B i.e., an aqueous medium—to encapsulate an immunostimulating agent within a polymeric shell for in vivo delivery. The ultrasound promotes crosslinking of the encapsulating agent by disulfide bonds to form the shell.

U.S. Pat. Nos. 5,981,719 and 6,268,053 disclose a method of preparing microparticles of macromolecules with particle size of less than 10 microns. Macromolecules are mixed with a soluble polymer or mixture of soluble polymers (e.g., albumin) at a pH near the isoelectric point of the macromolecule in the presence of an energy, preferably heat, for a predetermined length of time. The microparticles formed by this process allow aqueous fluids to enter and solubilized macromolecules and polymers to exit the microparticles and can be made to exhibit short-term or long-term release kinetics, thereby providing either rapid or sustained release of macromolecules.

SUMMARY OF THE INVENTION

One of the drawbacks of aqueous nanoparticle suspensions is their poor physical and chemical stability. Physical instability is due to particle aggregation and crystal growth. Chemical instability is due to degradation of the active ingredient solubilized in the surrounding solution that is in equilibrium with the suspended solid phase, which can be enhanced due to interactions of active ingredient with excipients such as the surfactants and buffers. Because of these stability problems, many aqueous nanoparticle systems are not suitable for use as pharmaceutical preparations. For example, if the dissolved active compound is chemically unstable due to hydrolysis, for example, then decomposition in solution would shift chemical equilibrium toward progressive degradation and loss of the active ingredient.

We have discovered that freezing may circumvent these instability mechanisms by encasing the drug particles in a frozen aqueous matrix. At such low temperatures, drug solubility is reduced and very high viscosity of the aqueous medium disfavors diffusion of solute drug away from the solid particle. This includes nucleation, crystal growth and Ostwald ripening. Lower temperatures also slow down the spontaneous degradation of the drug molecules in the aqueous medium to improve their chemical stability. Low temperatures also slow down the degradation of the active ingredient due to its interactions with the excipients. Crystallization of water may also occur, for example below the eutectic point of the mixture, thus eliminating the possibility of forming a solution phase containing drug which can undergo secondary nucleation, crystal growth and Ostwald ripening.

The present invention provides a composition of a stable nanoparticle suspension of a poorly water soluble pharmaceutical agent in an aqueous matrix and a method for preparing the composition. The present invention contemplates providing a stable suspension of other compounds such as cosmetics, photographically useful agents and the like. The composition can be stored for a prolonged period of time, preferably six months or longer.

The invention can be applied to any nanoparticle systems known in the art. The nanoparticle suspensions can be prepared from any of the known methods such as physical grinding, homogenization, high shear mixing, emulsion evaporation precipitation, solvent anti-solvent precipitation, supercritical fluid precipitation, temperature shift precipitation, pH shift precipitation, melt precipitation, and seeding.

The invention is also applicable to nanoparticle systems with a wide range of compositions including, for example, surface modifiers, pH adjusting agents, crystal growth modifiers, cryopreservation agents, osmotic agents, co-solvents and viscosity modulating agents.

The composition does not require reconstitution with an appropriate dispersing agent before use and is applicable to a variety of routes of administration including, but not limited to, injection (intravenous, intramuscular, subcutaneous), pulmonary, ophthalmic, topical and oral.

These and other aspects and attributes of the present invention will be discussed with reference to the following drawings and accompanying specification.

DETAILED DESCRIPTION OF THE INVENTION

While this invention is susceptible of embodiments in many different forms, and will herein be described in detail, preferred embodiments of the invention are disclosed with the understanding that the present disclosure is to be considered as exemplifications of the principles of the invention and are not intended to limit the broad aspects of the invention to the embodiments illustrated.

The present invention discloses a pharmaceutical composition for intraveneous or oral administration of and a method for preparing the composition as a nanoparticle suspension in an aqueous matrix. Parenteral administration includes intravenous, intra-arterial, intrathecal, intraperitoneal, intraocular, intra-articular, intradural, intramuscular, intradermal or subcutaneous injection. The composition is also suitable for other non-oral routes of administration including, for example, topical, ophthalmic, nasal, buccal, inhalation, rectal, and the like.

The pharmaceutical agent is preferably a poorly water soluble compound. The composition is physically and chemically unstable when stored in the refrigerator or at room temperature for a prolonged period of time, preferably for one year or longer. Stabilization can be accomplished by freezing the aqueous nanoparticle suspension and storing the composition in the frozen state. At such low temperatures, drug solubility is reduced and the very high viscosity of the aqueous medium disfavors diffusion of a solute drug away from a solid particle containing the drug. This includes nucleation, crystal growth and Ostwald ripening. Lower temperatures also slow down the spontaneous degradation of the drug molecules in the aqueous medium to improve their chemical stability. Crystallization of water may also occur, for example below the eutectic point of the mixture, thus eliminating the possibility of forming a solution phase containing drug which can undergo secondary nucleation, crystal growth and Ostwald ripening.

The present invention can also be practiced with suspensions of other poorly water soluble materials that are not pharmaceutical agents, including, for example, photographically useful compounds.

A. Compositions of Nanoparticle Suspensions:

The composition of the invention comprises nanoparticles of a pharmaceutical agent suspended in a frozen aqueous matrix. One or more excipients can be included in the composition as desired, depending on the particular pharmaceutical agent, the method of preparing the nanoparticle suspension, and the route of administration.

1. Pharmaceutical Agents

The invention can be practiced with a wide variety of pharmaceutical agents which can be a therapeutic agent, a diagnostic agent, or a cosmetic. They include organic and inorganic compounds and biologics such as proteins, peptides, saccharides, polysaccharides, polypeptides, nucleotides, and oligonucleotides.

The pharmaceutical agent can exist in a crystalline phase or in a non-crystalline, amorphous phase. The agent is preferably poorly water soluble. By "poorly water soluble" it is meant that the pharmaceutical agent has a solubility in water of less than 10 mg/ml, and preferably less than 1 mg/ml. These poorly water soluble agents are most suitable for aqueous nanoparticle suspension preparations since there are limited alternatives of formulating these agents in an aqueous medium.

The present invention can also be practiced with water soluble pharmaceutical agents, by entrapping these pharmaceutical agents in a solid carrier matrix (for example, poly-lactate-polyglycolate copolymer, albumin, starch), or by encapsulating these agents in a surrounding vesicle that is impermeable to the pharmaceutical agent. This encapsulating vesicle can be a polymeric coating such as polyacrylate. Further, the nanoparticles and microparticles prepared from these water soluble pharmaceutical agents can be modified to improve chemical stability and control the pharmacokinetic properties of the agents by controlling the release of the agents from the particles. Examples of water soluble pharmaceutical agents include, but are not limited to, simple organic compounds, proteins, peptides, nucleotides, oligonucleotides, and carbohydrates.

The therapeutic agent can be selected from a variety of known classes of pharmaceuticals including, for example, analgesics, anti-inflammatory agents, antihelmintics, anti-arrhythmic agents, antibiotics (including penicillins), anticoagulants, antidepressants, antidiabetic agents, antiepileptics, antifungals, antihistamines, antihypertensive agents, antimuscarinic agents, antimycobacterial agents, antineoplastic agents, antiprotozoal agents, immunosuppressants, immunostimulants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (anti-parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, vaccines and xanthines.

Diagnostic agents include the x-ray imaging agent and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy)butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy)acetamide (WIN 12855); diethyl 2-(3,5-bis(acetamido)-2,4,6-triiodobenzoyloxy malonate (WIN 67721); ethyl 2-(3,5-bis(acetamido)-2,4,6-triiodobenzoyloxy)phenylacetate (WIN 67585); propanedioic acid, [[3,5-bis(acetylamino)-2,4,5-triiodobenzoyl]oxy]bis(1-methyl)ester (WIN 68165); and benzoic acid, 3,5-bis(acetylamino)-2,4,6-triodo-4-(ethyl-3-ethoxy-2-butenoate)ester (WIN 68209). Preferred contrast agents include those which are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Antineoplastic, or anticancer agents, include but are not limited to paclitaxel and derivative compounds, and other antineoplastics selected from the group consisting of alkaloids, antimetabolites, alkylating agents and antibiotics.

Preferred therapeutic or diagnostic agents include those intended for oral administration and intravenous administration. A description of these classes of therapeutic agents and diagnostic agents and a listing of species within each class can be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

A cosmetic agent is any active ingredient capable of having a cosmetic activity. Examples of these active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol and stearyl glycerate. The cosmetics are commercially available and/or can be prepared by techniques known in the art.

The pharmaceutical agent can be present in an amount of from about 0.01% to about 50%, more preferably from about 0.1% to about 30%, and most preferably from about 0.5% to about 5%, by weight of the composition.

2. Excipients

The excipients in the invention are optional. One or more excipients can be included in the composition. Examples of excipients include buffers, surface modifiers, pH adjusting agents, crystal growth modifiers, cryopreservation agents, osmotic agents, co-solvents, and viscosity modulating agents.

Suitable surface modifiers can preferably be selected from known organic and inorganic pharmaceutical excipients such as an anionic surfactant, a cationic surfactant, a nonionic surfactant or a biological, surface-active molecule.

Suitable anionic surfactants include but are not limited to potassium laurate, sodium lauryl sulfate, sodium dodecylsulfate, alkyl polyoxyethylene sulfates, sodium alginate, dioctyl sodium sulfosuccinate, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.). Suitable cationic surfactants include but are not limited to quaternary ammonium compounds, such as benzalkonium chloride, cetyltrimethylammonium bromide, lauryldimethylbenzylammonium chloride, acyl carnitine hydrochlorides, or alkyl pyridinium halides.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myrj), polyoxyethylene-derivatized lipids or phospholipids, sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), polaxamines, methylcellulose, hydroxycellulose, hydroxy propylcellulose, hydroxy propylmethylcellulose, noncrystalline cellulose, polysaccharides including starch and starch derivatives such as hydroxyethylstarch (HES), polyvinyl alcohol, and polyvinylpyrrolidone. In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface active biological molecules include such molecules as albumin, casein, heparin, hirudin or other appropriate proteins.

Other representative examples of surface modifiers include gelatin, casein, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986 which is incorporated herein by reference and made part hereof.

The surface modifiers are commercially available and/or can be prepared by techniques known in the art. Two or more surface modifiers can be used in combination.

Suitable pH adjusting agents include but are not limited to buffers, sodium hydroxide, hydrochloric acid, tris(hydroxymethyl)aminomethane (tris), citrate, acetate, lactate, meglumine, or the like. Buffers also include but not limited to amino acids such as glycine, leucine, alanine, lysine, or the like.

Suitable crystal growth modifiers are described in U.S. Pat. No. 5,665,331. A crystal growth modifier is defined as a compound that in the co-precipitation process incorporates into the structure of the microprecipitated crystals of the pharmaceutical agent, thereby hindering growth or enlargement of the microcrystalline precipitate, by the so called Ostwald ripening process. Some crystal growth modifiers may be structurally similar, on a molecular basis, to the pharmaceutical agent. Also suitable as crystal modifiers are polymers such as the crystallization inhibitor polyvinyl pyrrolidinone as disclosed in U.S. Pat. No. 4,826,689. Crystal growth modifiers may also act by forming a complex with the solute that is at supersaturation, and thereby preventing or inhibiting crystal nucleation and/or growth.

Cryoprotectants used in nanoparticle suspensions are disclosed in U.S. Pat. No. 5,302,401. In the '401 patent, cryoprotectants inhibit the agglomeration of nanoparticles during the process of lyophilization. Examples of suitable cryoprotectants include carbohydrates such as sucrose, xylose, glucose, and sugar alcohols such as mannitol and sorbitol, surface active agents such as the polysorbates (Tweens), as well as glycerol and dimethylsulfoxide. Cryoprotectants may also include water-soluble polymers such as polyvinylpyrolidinone (PVP), starch, and polyalkoxy ethers such as polyethylene glycols, polypropylene glycols, and poloxamers. Biologically derived cryoprotectants include albumin. Yet another class of cryoprotectant includes pegylated lipids, such as Solutol. A preferred cryoprotectant is a carbohydrate. A preferred carbohydrate is a monosaccharide or disaccharide. A preferred disaccharide is sucrose. Another preferred cryoprotectant includes polymers such as, but not limited to, those listed above. Yet another preferred cryoprotectant is albumin.

Viscosity modulating agents are agents that affect the viscosity of the composition. Examples of modulating agents are carbohydrates (e.g. celluloses, gums, sugars, sugar alcohols), polymers (e.g., poloxamers, poloxamines, polyvinylpyrrolidone), proteins (e.g. albumin, milk proteins). These agents are listed in the Handbook of Pharmaceutical Additives published by Gower, under the Section of *Thickeners, Viscosity control agents, Consistency regulators, Bodying agents, Antigellants*, which is incorporated herein by reference and made part hereof.

Suitable osmotic agents include sugars (e.g. dextrose, sucrose), sugar alcohols (e.g. mannitol, sorbitol), salts (e.g. sodium chloride), glycerol and glycerol derivatives and the like.

Examples of suitable co-solvents are ethyl alcohol, dimethyl sulfoxide, and N-methyl-2-pyrrolidinone (also called N-methyl-2-pyrrolidone). Other examples include lactic acid, acetic acid and other liquid carboxylic acids.

The excipient can be present in an amount from about 0.001% to about 20%, preferably from about 0.01% to about 5%, by weight of the composition.

The excipient(s) can be added to the aqueous medium in the process of preparing of the nanoparticles, or they can be added directly to the pharmaceutical agent before mixing with the aqueous medium. If the pharmaceutical agent is dissolved in an organic phase prior to mixing with an aqueous anti-solvent, the excipient(s) may be added to the organic phase prior to precipitation.

3. Particle Size and Shape of Nanoparticles

In this invention, particle size is measured by dynamic light scattering methods (e.g., photocorrelation spectroscopy, laser diffraction, low-angle laser light scattering (LALLS), medium-angle laser light scattering (MALLS), light obscuration methods (Coulter method, for example), rheology, or microscopy (light or electron) within the ranges set forth above). The invention is applicable to nanoparticle and microparticle suspensions of a wide range of particle sizes. The preferred average effective particle size of the particles is less than about 100 µm, more preferably less than about 7 µm, more preferably less than about 2 µm, and most preferably less than about 400 µm and even more preferably less than about 200 nm or any range or combination of ranges therein.

4. Methods of Preparing Nanoparticle Suspensions

Aqueous nanoparticle suspensions of the pharmaceutical agent can be prepared by any method including mechanical grinding of the active agent, by precipitation techniques or by methods of suspending the pharmaceutical agent. Mechanical grinding include such techniques as jet milling, pearl milling, ball milling, hammer milling, fluid energy milling or wet grinding techniques such as those disclosed in U.S. Pat. No. 5,145,684, which is incorporated herein by reference and made a part hereof.

The precipitation step can be used to make a particle suspension that is further subjected to an energy-addition step. The energy-addition step includes subjecting the particle dispersion to high shear conditions including cavitation, shearing or impact forces utilizing a microfluidizer, piston gap homogenizer or counter-current flow homogenizer such as disclosed in U.S. Pat. No. 5,091,188 which is incorporated herein by reference and made a part hereof. Suitable piston gap homogenizers are commercially available such as those sold under the product name EMULSIFLEX by Avestin, and French Pressure Cells sold by Spectronic Instruments. Suitable microfluidizers are available from Microfluidics Corp. The crystal seeding step described below can be conducted at any point during the process of subjecting the solution to high shear conditions and most preferably is conducted prior to the energy addition step.

The step of adding energy can also be accomplished using sonication techniques. The step of sonicating can be carried out with any suitable sonication device such as the Branson Model S-450A or Cole-Parmer 500/750 Watt Model. Such devices are well-known in the industry. Typically the sonication device has a sonication horn or probe that is inserted into the drug containing solution to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as 1⁄2 inch or 1⁄4 inch or the like. It may also be desirable to cool the solution during sonication to temperatures below room temperature. The crystal seeding step described below can be conducted at any point during the process of subjecting the solution to high shear conditions and most preferably is conducted before the energy addition step.

The Method of Precipitation

In the method of precipitation, the pharmaceutical agent is dissolved in a solvent to derive a solution. The solution is then mixed with an aqueous medium to derive a pre-suspension of fine particles of the pharmaceutical agent. The aqueous medium may optionally contain one or more excipients selected from the group of surface modifiers, pH adjusting agents, cryoprotective agents, crystal growth modifiers, osmotic agents, co-solvents, and viscosity modifiers. The excipients may also be included in the solvent in which the pharmaceutical agent is dissolved, prior to the precipitation step. Energy can be applied to the pre-suspension as needed to stabilize a coating of the agent, to change the lattice structure, or to further reduce the size of the particles of the precipitate. Sources of energy include but not limited to sonication, homogenization, microfluidization, countercurrent homogenization, or other methods of providing impact, shear or cavitation forces. The energy sources also include methods for providing continuous thermal input in the form of heating or cooling, or by temperature variation (e.g., cycling).

Some known precipitation processes are emulsion evaporation precipitation, microprecipitation, solvent anti-solvent precipitation, supercritical fluid precipitation, temperature shift precipitation, pH shift precipitation, and seeding.

Emulsion Evaporation Precipitation

The method of emulsion evaporation is disclosed in U.S. patent application Ser. No. 09/964,273, which is incorporated herein by reference and made part hereof. The process comprises the steps of: (1) providing a multiphase system having an organic phase and an aqueous phase, the organic phase having a pharmaceutically effective compound therein; and (2) sonicating the system to evaporate a portion of the organic phase to cause precipitation of the compound in the aqueous phase and having an average effective particle size of less than about 2 µm. The step of providing a multiphase system includes the steps of: (1) mixing a water immiscible solvent (oil phase) with the pharmaceutically effective compound to define an organic solution, (2) preparing an aqueous based solution with one or more surface active compounds, and (3) mixing the organic solution with the aqueous solution to form the multiphase system. The multiphase system can be agitated or mixed to form a crude emulsion. The crude emulsion will have oil droplets in the water of a size of approximately less than about 1 µm in diameter. The crude emulsion is sonicated to define a microemulsion and eventually to define a submicron particle suspension.

The water immiscible solvent is selected from the group consisting of: linear, branched or cyclic alkanes with carbon number of 5 or higher, linear, branched or cyclic alkenes with carbon number of 5 or higher, linear, branched or cyclic alkynes with carbon number of 5 or higher; aromatic hydrocarbons completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents. A preferred water immiscible solvent is methylene chloride.

The sonicating step can be replaced by any other means of providing energy and examples of other sources of energy are sonication, homogenization, microfluidization, counter-current homogenization, or other methods of providing impact, shear or cavitation forces.

Microprecipitation

The method of microprecipitation is disclosed in U.S. Patent Application Ser. No. 60/258,160; 09/874,799; 09/874,637; 09/874,499; and 09/953,979. Small particles of organic compounds are formed by precipitating an organic compounds in an aqueous medium to form a pre-suspension followed by adding energy to stabilize a coating of the particle or to alter the lattice structure of the particle. The process is preferably used to prepare a suspension of a poorly water-soluble, pharmaceutically active compound suitable for parenteral or oral administration.

The process can be subdivided into two categories, Method A and Method B.

Method A

In Method A, the organic compound ("drug") is first dissolved in the first solvent to define a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solution is provided with one or more optional surface modifiers such as an anionic surfactant, a cationic surfactant, a nonionic surfactant or a biological surface active molecule added thereto.

It may also be desirable to add a pH adjusting agent to the second solution such as buffers, sodium hydroxide, hydrochloric acid, tris buffer, citrate, acetate, lactate, meglumine, or the like. Other buffers include amino acids such as glycine, leucine, alanine, lysine, and the like. The second solution should have a pH within the range of from about 2 to about 11.

In a preferred form of the invention, the method for preparing submicron sized particles of an organic compound includes the steps of adding the first solution to the second solution. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to define a pre-suspension. The method further includes the step of subjecting the pre-suspension to an annealing step to convert the amorphous particles, supercooled liquid or semi-crystalline solid to a crystalline more stable solid state. The resulting particles will have an average effective particle size as measured by dynamic light scattering methods (e.g., photocorrelation spectroscopy, laser diffraction, low-angle laser light scattering (LALLS), medium-angle laser light scattering (MALLS), light obscuration methods (Coulter method, for example), rheology, or microscopy (light or electron) within the ranges set forth above).

The energy-addition step involves adding energy through sonication, homogenization, countercurrent flow homogenization, microfluidization, or other methods of providing impact, shear or cavitation forces. The sample may be cooled or heated during this stage. In one preferred form of the invention the annealing step is effected by a piston gap homogenizer such as the one sold by Avestin Inc. under the product designation EmulsiFlex-C160. In another preferred form of the invention the annealing may be accomplished by ultrasonication using an ultrasonic processor such as the Vibra-Cell Ultrasonic Processor (600W), manufactured by Sonics and Materials, Inc. In yet another preferred form of the invention, the annealing may be accomplished by use of an emulsification apparatus as described in U.S. Pat. No. 5,720,551 which is incorporated herein by reference and made a part hereof.

Depending upon the rate of annealing, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the annealing step.

In addition to amorphous particles, semi-crystalline solids, or a supercooled liquid, the pre-suspension may also consist of friable crystals that are more easily comminuted than in their solid state prior to precipitation. In this case, the energy-addition step breaks down these particles to a desired size.

Method B

Method B differs from Method A in the following respects. The first difference is a surfactant or combination of surfactants is added to the first solution. The surfactants may be selected from the groups of nonionic, anionic, and cationic surfactants.

In addition to amorphous particles, semi-crystalline solids, or a supercooled liquid, the pre-suspension may also consist of friable crystals that are more easily comminuted than in their solid state prior to precipitation. In this case, the energy-addition step breaks down these particles to a desired size.

One suitable emulsion precipitation technique is disclosed in the co-pending and commonly assigned U.S. Ser. No. 09/964,273, which is incorporated herein by reference and is made a part hereof. In this approach, the process includes the steps of: (1) providing a multiphase system having an organic phase and an aqueous phase, the organic phase having a pharmaceutically effective compound therein; and (2) sonicating the system to evaporate a portion of the organic phase to cause precipitation of the compound in the aqueous phase and having an average effective particle size of less than about 2 μm. The step of providing a multiphase system includes the steps of: (1) mixing a water immiscible solvent with the pharmaceutically effective compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 μm in diameter. The crude emulsion is sonicated to define a microemulsion and eventually to define a submicron sized particle suspension.

An optional polymorph control step discussed in detail below can be conducted during any of these steps. The polymorph control step can be taken prior to, or after sonicating the system. In a most preferred form of the invention, the polymorph control step is conducted during the sonicating step.

Another approach to preparing submicron sized particles is disclosed in co-pending and commonly assigned U.S. Ser. No. 10/183,035, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain submicron sized particles of the pharmaceutical compound. The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

The polymorph control step discussed in detail below can be conducted during any of these steps. In a most preferred form of the invention, the polymorph control step is conducted at the mixing step (3) of the step of providing a multiphase system.

Solvent Anti-solvent Precipitation

A suitable solvent anti-solvent precipitation technique is disclosed in U.S. Pat. Nos. 5,118,528 and 5,100,591 which are incorporated herein by reference and made a part hereof. The process includes the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a colloidal suspension of nanoparticles. The '528 patent discloses that it produces particles of the substance smaller than 500 nm without the supply of energy.

As above, an optional polymorph control step discussed in detail below can be conducted during any of these steps. In a most preferred form of the invention, the polymorph control step is conducted at step (3) prior to adding together the solutions (1) and (2).

Phase Inversion Precipitation

One suitable phase inversion precipitation is disclosed in U.S. Pat. Nos. 6,235,224, 6,143,211 and U.S. Patent Application No. 2001/0042932 which are incorporated herein by reference and made a part hereof. Phase inversion is a term used to describe the physical phenomena by which a polymer dissolved in a continuous phase solvent system inverts into a solid macromolecular network in which the polymer is the continuous phase. One method to induce phase inversion is by the addition of a non-solvent to the continuous phase. The polymer undergoes a transition from a single phase to an unstable two phase mixture: polymer rich and polymer poor fractions. Micellar droplets of non-solvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For an optional polymorph control step to be effective in this process it is desirable the agent is dissolved in the solvent. The polymer, the agent and the solvent together form a mixture having a continuous phase, wherein the solvent is the continuous phase. The mixture is then introduced into at least tenfold excess of a miscible non-solvent to cause the spontaneous formation of the microencapsulated microparticles of the agent having an average particle size of between 10 nm and 10 µm. The particle size is influenced by the solvent:non-solvent volume ratio, polymer concentration, the viscosity of the polymer-solvent solution, the molecular weight of the polymer, and the characteristics of the solvent-non-solvent pair. The process eliminates the step of creating microdroplets, such as by forming an emulsion, of the solvent. The process also avoids the agitation and/or shear forces.

The optional polymorph control step discussed in detail below can be conducted during any of these steps. In a most preferred form of the invention, the polymorph control step is conducted prior to or during the adding of the non-solvent to the continuous phase.

pH Shift Precipitation pH shift precipitation techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a pre-suspension of submicron sized particles of the pharmaceutically active compound. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a fine particle dispersion of the pharmaceutical agent. The precipitation step can be followed by steps of diafiltration clean-up of the dispersion and then adjusting the concentration of the dispersion to a desired level. This process of reportedly leads to microcrystalline particles of Z-average diameters smaller than 400 nm as measured by photon correlation spectroscopy.

The optional polymorph control step discussed in detail below can be conducted during any of these steps. In a preferred form of the invention, the polymorph control step is conducted prior to or during the neutralizing step.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method

Suitable infusion precipitation techniques are disclosed in the U.S. Pat. Nos. 4,997,454 and 4,826,689, which are incorporated herein by reference and made a part hereof. First, a suitable solid compound is dissolved in a suitable organic solvent to form a solvent mixture. Then, a precipitating non-solvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 µm. Agitation (e.g., by stirring) of the solution being infused with the precipitating non-solvent is preferred. The non-solvent may contain a surfactant to stabilize the particles against aggregation. The particles are then separated from the solvent. Depending on the solid compound and the desired particle size, the parameters of temperature, ratio of non-solvent to solvent, infusion rate, stir rate, and volume can be varied according to the invention. The particle size is proportional to the ratio of non-solvent:solvent volumes and the temperature of infusion and is inversely proportional to the infusion rate and the stirring rate. The precipitating non-solvent may be aqueous or non-aqueous, depending upon the relative solubility of the compound and the desired suspending vehicle.

The optional polymorph control step discussed in detail below can be conducted during any of these steps. In a preferred form of the invention, the polymorph control step is conducted prior to or during the infusion of the non-solvent.

Temperature Shift Precipitation

Temperature shift precipitation technique, also known as the hot-melt technique, is disclosed in U.S. Pat. No. 5,188, 837 to Domb, which is incorporated herein by reference and made a part hereof. In an embodiment of the invention, lipospheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

The optional polymorph control step discussed in detail below can be conducted during any of these steps provided that the processing temperatures do not exceed the melting point of the drug. In a most preferred form of the invention, the polymorph control step is conducted before the step of cooling the warm drug dispersion.

Solvent Evaporation Precipitation

Solvent evaporation precipitation techniques are disclosed in U.S. Pat. No. 4,973,465 which is incorporated herein by reference and made a part hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring. The solvent can be removed by adding energy to the solution to evaporate a sufficient quantity of the solvent to cause precipitation of the compound. The solvent can also be removed by other well known techniques such as applying a vacuum to the solution or blowing nitrogen over the solution. The optional polymorph control step discussed in detail below can be conducted during any of these steps. In a most preferred form of the invention, the polymorph control step is conducted prior to the evaporation step.

Reaction Precipitation

Reaction precipitation includes the steps of dissolving the pharmaceutical compound into a suitable solvent to form a solution. The compound should be added in an amount at or below the saturation point of the compound in the solvent. The compound is modified by reacting with a chemical agent or by modification in response to adding energy such as heat or UV light or the like to such that the modified compound has a lower solubility in the solvent and precipitates from the solution. The optional polymorph control step discussed in detail below can be conducted during any of these steps. In a most preferred form of the invention, the polymorph control step is conducted prior to or during the precipitation step.

Compressed Fluid Precipitation

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an anti-solvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as fine particles in the aqueous phase. In this case, the compressed fluid acts as a solvent.

In order to stabilize the particles against aggregation, a surface modifier, such as a surfactant, is included in this technique. Particles prepared by this technique are generally 500 nm or smaller.

The optional polymorph control step discussed in detail below can be conducted during any of these steps. In a most preferred form of the invention, the polymorph control step is conducted prior to or during the particle formation step.

The Method of Suspension

The other method of preparing aqueous nanoparticle suspensions is the method of suspension. In this method, particles of the pharmaceutical agent are dispersed in an aqueous medium by adding the particles directly into the aqueous medium to derive a pre-suspension. The particles are normally coated with a surface modifier to inhibit the aggregation of the particles. One or more other excipients can be added either to the pharmaceutical agent or to the aqueous medium.

Energy may be added to the pharmaceutical agent or the pre-suspension to reduce the sizes of the particles of the pharmaceutical agents to the desired particle size. Examples of sources of energy include but not limited to sonication, homogenization, microfluidization, counter current homogenization, or other methods of providing impact, shear or cavitation forces.

Polymorph Control

The methods of preparing a suspension can further include the step of crystal seeding to control the crystal structure of the drug. What is meant by the term "crystal structure" is the arrangement and/or conformation of the molecules within the crystal lattice. Compounds that can be crystallized into different crystal structures are said to be polymorphic. Identification of polymorphs is an important step in drug formulation since different polymorphs of the same drug can show differences in solubility, therapeutic activity, bioavailability, and suspension stability. Similarly, different polymorphs of the same excipient can show differences in solubility, compatibility with the drug to be delivered, chemical stability and suspension stability. Accordingly, it is important to control the polymorphic form of the compound for ensuring product purity and batch-to-batch reproducibility.

The polymorphic form of the compound in the process discussed above can be controlled by the additional step of seeding. Seeding includes using a seed compound or adding energy to form a seed compound. In a preferred form of the invention, the seed compound is the pharmaceutically-active compound in the desired polymorphic form. Alternatively, the seed compound can also be an inert impurity or an organic compound with a structure similar to that of the desired polymorph.

The seed compound can be precipitated from a drug containing solution of any of the above-described processes. This method includes the steps of adding the pharmaceutically-active compound in sufficient quantity to exceed the solubility of the pharmaceutically-active compound in the first solution to create a supersaturated solution. The supersaturated solution is treated to precipitate the pharmaceutically-active compound in the desired polymorphic form. Treating the supersaturated solution includes aging the solution for a time period until the formation of a crystal or crystals is observed to create a seeding mixture. Treating the solution also includes subjecting the solution to temperature shifting or pH shifting. It is also possible to add energy to the supersaturated solution to cause the pharmaceutically-active compound to precipitate out of the solution in the desired polymorph. The energy can be added in a variety of ways including the energy addition steps described above. Further energy can be added by heating or exposing the pre-suspension to electromagnetic energy, particle beam or electron beam sources. The electromagnetic energy includes using a laser beam, dynamic electromagnetic energy, or other radiation sources. It is further contemplated utilizing ultrasound, static electric field and a static magnetic field as the energy addition source.

In a preferred form of the invention, the method for producing seed crystals from an aged supersaturated solution includes the steps of: (i) adding a quantity of the pharmaceutically-active compound to a drug solution to create a supersaturated solution, (ii) aging the supersaturated solution to form detectable crystals to create a seeding mixture; and (iii) precipitating the seeding mixture to create a pre-suspension. The pre-suspension can then be further processed as described herein to provide an aqueous suspension of the pharmaceutically-active compound in the desired polymorph and in the desired size range.

Seeding can also be accomplished by adding energy to the first solution or the pre-suspension to form seed compound provided that the exposed liquid or liquids contain the pharmaceutical compound or a seed material. The energy can be added in the same fashion as described above for the supersaturated solution.

Accordingly, the present invention provides a composition of matter of a pharmaceutical compound in a desired polymorphic form essentially free of the unspecified polymorph or polymorphs. It is contemplated the methods of this invention can apply used to selectively produce a desired polymorph for numerous pharmaceutical compounds.

6. Sterilization of the Composition

The composition can be heat sterilized or filtered then aseptic processed before freezing, depending on the thermal stability of the particular components of the composition and on the particle size of the composition. The preferred method for the production of a sterile product is to filter selected components followed by an aseptic process of manufacture prior to freezing. An alternate method of sterilization for the invention is by gamma irradiation before or after the freezing step.

EXAMPLES

Example 1

Preparation of Itraconazole Suspension by Use of Microprecipitation Method A with Homogenization Followed by Freezing the Suspension Surfactant Solution: To a 4 L flask add 3500 mL of distilled water, 22 g of glycerin, 22 g of poloxamer 407, and 22 g of poloxamer 188. The surfactant solution was heated and stirred to dissolve the solids. The surfactant solution was cooled and diluted to 4 liters with distilled water.

Itraconazole Concentrate: In a 100 mL beaker, 15 g itraconazole and 67.5 g of lactic acid were combined. The mixture was heated to dissolve the solids. The itraconazole concentrate was cooled to room temperature.

Pre-suspension: The itraconazole concentrate was transferred to a 60 mL syringe. 1.5 liters of surfactant solution was transferred to a jacketed homogenizer hopper. An overhead stirrer was positioned into the diluent solution until the mixing blades were fully immersed. Using a syringe pump, the itraconazole concentrate was added slowly to the diluent solution with mixing.

Homogenized suspension: The pre-suspension was immediately homogenized (10,000 psi) for approximately 20 minutes.

Final suspension: The excess lactic acid was removed by centrifuging the homogenized suspension for 20 minutes. The supernatant was discarded and the solids were re-suspended in a surfactant solution consisting of fresh surfactant solution. The suspension was mixed then centrifuged for 20 minutes. The supernatant was discarded and the solids were re-suspended in a surfactant solution consisting of fresh surfactant solution. The re-suspended sample was homogenized for approximately 20 minutes at 10,000 psi. The final pH of the suspension was approximately 4. The suspension was collected into 50 mL bottles and sealed with Teflon® faced stoppers.

Frozen suspension: 3–50 mL samples of the final suspension was put into a −20° C. freezer and 3–50 mL samples of the final suspension were stored at 2–8° C. After approximately 1 month the samples were removed from −20° C. storage and allowed to thaw under ambient conditions. The samples were transferred to 2–8° C. No phase separation, visible aggregation or caking was observed. The sample, which was subjected to freezing and the controls, which was stored at 2–8° C. and were tested for particle size distribution by laser light scattering. There were no discernable differences in the particle size distribution between the frozen samples and the controls (see below).

| Sample ID | Mean Particle Size | 99% Particle Size |
|---|---|---|
| Control-1 | 0.243 | 0.510 |
| Control-1 1 min sonication | 0.238 | 0.510 |
| Control-2 | 0.240 | 0.510 |
| Control-2 1 min sonication | 0.247 | 0.510 |
| Control-3 | 0.250 | 0.510 |
| Control-3 1 min sonication | 0.266 | 0.510 |
| Freeze-1 | 0.246 | 0.510 |
| Freeze-1 1 min sonication | 0.261 | 0.510 |
| Freeze-2 | 0.232 | 0.510 |
| Freeze-2 1 min sonication | 0.245 | 0.510 |
| Freeze-3 | 0.236 | 0.510 |
| Freeze-3 1 min sonication | 0.241 | 0.510 |

It is reasonable to project that the frozen suspension to be stable for one year or longer under these storage conditions.

Example 2

Amorphous Itraconazole Nanosuspensions are Stabilized by Storage at −70° C.

Itraconazole (4.0 grams) was dissolved in 20 mL of methylene chloride and combined with 400 mL of 5% albumin solution (diluted from 25%). The combined solutions were manually shaken to effect dispersion of the two liquids. The crude emulsion was than sonicated (T=5° C.), for 6 minutes (sonicating every other 30 seconds using a 1" probe at 40% amplitude). The sonicated solution was rotovapped under house vacuum (~100 torr) for about ½ hour, and than under pump vacuum (<20 torr) for about 2 hours. The rotovapped product was analyzed by light scattering detection (Horiba) which revealed particles having a mean diameter of 406 nm. This product was then sent to Galbraith Laboratories, Inc. for GC headspace analysis, which revealed the methylene chloride concentration to be 12.3 ppm. Inspection by visible light microscopy showed the particles to be spherical in shape with no evidence of crystallinity. Additionally, x-ray powder diffraction analysis on particles produced by this method confirmed them to be completely amorphous.

Approximately 35 mL of the product was stored at −70 degrees Celsius for 32 days. Re-analysis of the suspension by HORIBA light scattering detection and microscopic examination revealed essentially no change in particle size (mean value of 427 nm). It is reasonable to project that the frozen suspension to be stable for one year or longer under these storage conditions.

Example 3

1% Budesonide in a PEG-Phospholipid Surfactant System

Ingredients:
1% budesonide
1.2% mPEG-PSPE, MW 2000
2.25% glycerin
0.14% sodium phosphate dibasic A weighed quantity of mPEG-PSPE (palmitoyl-stearoyl-phosphatidylethanolamine) and a volume of a previously prepared aqueous solution containing 2.25% glycerin and 0.14% sodium phosphate dibasic at pH 8.6 were combined and mixed using a high-shear mixer. Drug material was added and the blend was mixed under high shear to form a pre-suspension. The pre-suspension was homogenized for 30 discrete passes at a pressure of 25,000 psi.

A portion of the sample was frozen at −20° C. for 24 hours, and then allowed to thaw completely at room temperature.

Particle Size Results (Measured by Laser Diffractometry)

| Diameter (Volume-Weighted) | Initial (microns) | After Freeze-Thaw (microns) |
|---|---|---|
| Mean | 0.8472 | 0.8371 |
| 99th percentile | 1.688 | 1.685 |

Example 4

1% Nabumetone with Albumin Surfactant Ingredients

5% human albumin
1% nabumetone

A volume of albumin solution and a weighed quantity of the drug material were combined and mixed under high shear to form a pre-suspension. The pre-suspension was homogenized for 30 discrete passes at a pressure of 25,000 psi.

A portion of the sample was homogenized at −20° C. for 24 hours, and then allowed to thaw completely at room temperature.

Particle Size Results (Measured by Laser Diffractometry)

| Diameter (Volume-Weighted) | Initial (microns) | After Freeze-Thaw (microns) |
|---|---|---|
| Mean | 0.7721 | 0.7940 |
| 99th percentile | 1.889 | 1.936 |

Example 5

1% Nabumetone with Polyalkoxyether Surfactant and Bile Salt Ingredients 2.2% Poloxamer 188
0.1% sodium deoxycholate
2.2% glycerin
1% nabumetone A weighed quantity of the drug material and a volume of a solution containing 2.2% Poloxamer 188, 0.1% sodium deoxycholate, and 2.2% glycerin adjusted to pH 8.7 were combined and mixed under high shear to form a pre-suspension. The pre-suspension was homogenized for 20 discrete passes at a pressure of 25,000 psi.

A portion of the sample was frozen at −20° C. for 24 hours, and then allowed to thaw completely at room temperature.

Particle Size Results (Measured by Laser Diffractometry)

| Diameter (Volume-Weighted) | Initial (microns) | After Freeze-Thaw (microns) |
|---|---|---|
| Mean | 1.0498 | 1.085 |
| 99th percentile | 2.423 | 2.484 |

Example 6

1% Budesonide with PEG-Fatty Acid Ester Ingredients 0.125% Solutol
2.25% glycerin
1% budesonide A weighed quantity of the drug material and a volume of a solution containing 0.125% solutol, and 2.25% glycerin adjusted to pH 8.7 were combined and subjected to high shear mixing to form a pre-suspension. The pre-suspension was homogenized for 30 discrete passes at a pressure of 25,000 psi.

A portion of the sample was frozen at −20° C. for 24 hours, and then allowed to thaw completely at room temperature.

Particle Size Results (Measured by Laser Diffractometry)

| Diameter (Volume-Weighted) | Initial (microns) | After Freeze-Thaw (microns) |
|---|---|---|
| Mean | 0.7587 | 0.7641 |
| 99th percentile | 1.460 | 1.480 |

Example 7

1% Vitamin E TPGS (d-alpha tocopheryl polyethylene glycol 1000 succinate)
1% Nabumetone
2.25% Glycerin
0.14% sodium phosphate dibasic Combined a weighed quantity of Vitamin E TPGS and a volume of a premade aqueous solution containing 2.25% glycerin and 0.14% sodium phosphate dibasic at pH 8.6. Stirred the mixture by vortex until the Vitamin E TPGS dissolved. Added the drug material and Ultraturraxed the mixture to form a pre-suspension. Homogenized the pre-suspension with an Avestin B3 homogenizer for 30 discrete passes at a pressure of 25 kpsi.

Froze a portion of the sample at −20° C. for 24 hours, then allowed it to thaw completely at room temperature.

Particle Size Results

| | Initial | Freeze-Thaw |
|---|---|---|
| Unsonicated 99th% ile | 2.372 m | 2.593 m |
| Sonicated 99th% ile | 2.266 m | 2.398 m |
| Sonicated mean | 1.0332 m | 1.0333 m |

While specific embodiments have been illustrated and described, numerous modifications come to mind without departing from the spirit of the invention and the scope of the protection is only limited by the scope of the accompanying claims.

We claim:

1. A composition comprising a suspension of particles of a crystalline phase pharmaceutical agent or an amorphous phase pharmaceutical agent in a frozen aqueous matrix, the pharmaceutical agent selected from the group consisting of itraconazole, nabumetone and budesonide, wherein the pharmaceutical agent has a solubility in water of less than 10.0 mg/ml and the particle size of the pharmaceutical agent is about 50 nm to 50 microns.

2. The composition according to claim 1, wherein the pharmaceutical agent is present in an amount of from about 0.01 to about 50% by weight based on the total weight of the composition.

3. The composition according to claim 1, wherein the mean diameter of the particles of the pharmaceutical agent is about 50 nm to 2 microns.

4. The composition according to claim 1, wherein about over 99% of the particles have particle size of less than about 5 microns.

5. The composition according to claim 1, further comprising one or more excipients selected from the group consisting of: surface modifiers, pH adjusting agents, crystal growth modifiers, cryopreservation agents, osmotic agents, co-solvents, and viscosity modulating agents.

6. The composition according to claim 5, wherein the surface modifier is selected from the group consisting of: anionic surfactants, cationic surfactants, nonionic surfactants and surface active biological modifiers.

7. The composition according to claim 6, wherein the nonionic surfactant is selected from the group consisting of: polyoxyethylene fatty alcohol ethers, polyoxyethylene sorbitan fatty acid esters, polyoxyethylene fatty acid esters, polyoxyethylene-derivatized lipids such as Mpeg-PSPC (palmitoyl-stearoyl-phophatidylcholine), Mpeg-PSPE (palmitoyl-stearoyl-phophatidylethanolamine), sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

8. The composition according to claim 6, wherein the anionic surfactant is selected from the group consisting of: potassium laurate, triethanolamine stearate, sodium lauryl sulfate, sodium dodecylsulfate, alkyl polyoxyethylene sulfates, sodium alginate, dioctyl sodium sulfosuccinate, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

9. The composition according to claim 6, wherein the cationic surfactant is selected from the group consisting of quaternary ammonium compounds, benzalkonium chloride, cetyltrimethylammonium bromide, chitosans and lauryldimethylbenzylammonium chloride.

10. The composition according to claim 6, wherein the surface active biological modifiers are selected from the group consisting of: albumin, casein, heparin, hirudin, or other proteins.

11. The composition according to claim 5, wherein the pH adjusting agent is selected from the group consisting of: buffers, sodium hydroxide, hydrochloric acid, tris, citrate, acetate, lactate, meglumine, amino acids selected from the group consisting of glycine, alanine, leucine, isoleucine, lysine, methionine, tyrosine, phenylalanine, tryptophan, histidine, proline, serine, glutamic acid, aspartic acid, asparagine, glutamine, cysteine, and taurine.

12. The composition according to claim 5, wherein the cryopreservation agent is selected from the group consisting of carbohydrates, glycerol, polyalkoxyethers, PEG-fatty acids and lipids, biologically-based surfactants, and other surface active agents.

13. The composition according to claim 12, wherein the carbohydrate is selected from the group consisting of saccharides, disaccharides, and sugar alcohols.

14. The composition according to claim 13, wherein the disaccharide is sucrose.

15. The composition according to claim 13, wherein the sugar alcohol is mannitol.

16. The composition according to claim 12, wherein the surface active agent is selected from the group consisting of polysorbate (Tweens), glycerol, polyalkoxyethers, PEG-fatty acids, PEG-lipids, albumin, starch, and dimethylsulfoxide.

17. The composition according to claim 5, wherein the viscosity modulating agent is selected from the group consisting of carbohydrates, polymers, and proteins.

18. The composition according to claim 5, wherein the excipient is present in an amount of from about 0.001% to about 20% based on the total weight of the composition.

19. The composition according to claim 5, wherein the excipient is present in an amount of from about 0.01% to about 5% based on the total weight of the composition.

20. The composition according to claim 1, wherein the suspension is stable for at least 6 months.

21. A method for stabilizing a suspension of a crystalline phase pharmaceutical agent or an amorphous phase pharmaceutical agent in an aqueous matrix, the pharmaceutical agent being selected from the group consisting of itraconazole, nabumetone and budesonide, the method comprising the steps of:
providing the suspension in an aqueous matrix; and
freezing the aqueous suspension,
wherein the pharmaceutical agent has a solubility in water of less than 10.0 mg/ml and the particle size of the pharmaceutical agent is about 50 nm to 50 microns.

22. The method according to claim 21, wherein the pharmaceutical agent is present in an amount of from about 0.01 to about 50% by weight based on the total weight of the composition.

23. The method according to claim 21, wherein the mean diameter of the particles of the pharmaceutical agent is about 50 nm to 2 microns.

24. The method according to claim 21, wherein about over 99% of the particles have particle size of less than about 5 microns.

25. The method according to claim 21, further comprising the step of sterilizing by filter sterilization before freezing.

26. The method according to claim 21, further comprising the step of sterilizing by heat sterilization before freezing.

27. The method according to claim 21, further comprising the step of sterilization by gamma-irradiation.

28. The method according to claim 21, wherein the step of providing the suspension is a method selected from the group consisting of: precipitating the pharmaceutical agent in an aqueous medium to derive a pre-suspension; and suspending the pharmaceutical agent in an aqueous medium to derive a pre-suspension.

29. The method according to claim 28, wherein the step of precipitating is selected from the group consisting of: microprecipitation, emulsion evaporation, solvent anti-solvent precipitation, supercritical fluid precipitation, temperature shift precipitation, pH shift precipitation, and seeding.

30. The method according to claim 28, wherein the step of suspending comprises adding the pharmaceutical agent to the aqueous medium.

31. The method according to claim 30, further comprising the step of adding energy to the pharmaceutical agent or to the pre-suspension.

32. The method according to claim 31, wherein the step of adding energy to the pharmaceutical agent comprises performing a method selected from the group consisting of sonication, homogenization, microfluidization, countercurrent homogenization, and methods of providing impact, shear or cavitation forces, or thermal energy input, either in a continuous fashion, or by temperature variation.

33. The method according to claim 31, wherein the pharmaceutical agent has particles of a first average particle size prior to the energy-addition step and a second average particle size after the energy-addition step wherein the second average particle size is less than the first average particle size.

34. The method according to claim 28, wherein the pre-suspension further comprising one or more excipients selected from the group consisting of: surface modifiers, pH adjusting agents, crystal growth modifiers, cryopreservation agents, osmotic agents, co-solvents and viscosity modulating agents.

35. The method according to claim 34, wherein the surface modifier is selected from the group consisting of: anionic surfactants, cationic surfactants, nonionic surfactants and surface active biological modifiers.

36. The method according to claim 33, wherein the nonionic surfactant is selected from the group consisting of: polyoxyethylene fatty alcohol ethers, polyoxyethylene sorbitan fatty acid esters, polyoxyethylene fatty acid esters, polyoxyethylene-derivatized lipids such as Mpeg-PSPC (palmitoyl-stearoyl-phophatidylcholine), Mpeg-PSPE (palmitoyl-stearoyl-phophatidylethanolamine), sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

37. The method according to claim 35, wherein the anionic surfactant is selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

38. The method according to claim 35, wherein the cationic surfactant is selected from the group consisting of quaternary ammonium compounds, benzalkonium chloride, cetyltrimethylanimonium bromide, chitosans and lauryldimethylbenzylammonium chloride.

39. The method of claim 35, wherein the surface active biological modifiers are selected from the group consisting of: albumin, casein, heparin, hirudin, or other proteins.

40. The method according to claim 34, wherein the pH adjusting agent is selected from the group consisting of: sodium hydroxide, buffers, hydrochloric acid, tris, citrate, acetate, lactate, meglumineand amino acids selected from the group glycine, alanine, leucine, isoleucine, lysine, methionine, tyrosine, phenylalanine, tryptophan, histidine, proline, serine, glutamic acid, aspartic acid, asparagine, glutamine, cysteine, and taurine.

41. The method according to claim 34, wherein the cryopreservation agent is selected from the group consisting of carbohydrates, glycerol, polyalkoxyethers, PEG-fatty acids and lipids, biologically-based surfactants, and other surface active agents.

42. The method according to claim 41, wherein the carbohydrate is selected from the group consisting of saccharides, disaccharides, and sugar alcohols.

43. The method according to claim 42, wherein the disaccharide is sucrose.

44. The method according to claim 42, wherein the sugar alcohol is mannitol.

45. The method according to claim 41, wherein the surface active agent is selected from the group consisting of polysorbates (Tweens), glycerol, polyalkoxyethers, PEG-fatty acids, PEG-lipids, albumin, starch, and dimethylsulfoxide.

46. The method according to claim 34, wherein the viscosity-modulating agent is selected from the group consisting of carbohydrates, polymers, and proteins.

47. The method according to claim 34, wherein the excipient is present in an amount of about 0.001% to about 20% based on the total weight of the pre-suspension.

48. The method according to claim 34, wherein the excipient is present in an amount of about 0.01% to about 5% based on the total weight of the pre-suspension.

49. The method according to claim 31, wherein the step of adding energy to the pre-suspension comprises the step of performing a method selected from the group consisting of sonication, homogenization, microfluidization, countercurrent homogenization, and methods of providing impact, shear or cavitation forces, or thermal energy input, either in a continuous fashion, or by temperature variation.

50. The method according to claim 29, wherein the emulsion evaporation method comprises the steps of: dissolving the pharmaceutical agent in a volatile water immiscible solvent to form a solution; combining the solution with an aqueous medium to form an emulsion; mixing the emulsion to form a microemulsion; and removing the volatile water immiscible solvent in the microemulsion to form an aqueous suspension.

51. The method according to claim 50, wherein the aqueous suspension further comprises one or more excipients selected from the group consisting of surface modifiers, pH adjusting agents, crystal growth modifiers, cryopreservation agents, osmotic agents, co-solvents, and viscosity modulating agent.

52. The method according to claim 51, wherein the surface modifier is selected from the group consisting of: anionic surfactants, cationic surfactants, nonionic surfactants and surface active biological modifiers.

53. The method according to claim 52, wherein the nonionic surfactant is selected from the group consisting of: polyoxyethylene fatty alcohol ethers, polyoxyethylene sorbitan fatty acid esters, polyoxyethylene fatty acid esters, polyoxyethylene-derivatized lipids such as Mpeg-PSPC (palmitoyl-stearoyl-phophatidylcholine), Mpeg-PSPE (palmitoyl-stearoyl-phophatidylethanolamine), sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

54. The method according to claim 52, wherein the anionic surfactant is selected from the group consisting of: potassium laurate, triethanolamine stearate, sodium lauryl sulfate, sodium dodecylsulfate, alkyl polyoxyethylene sulfates, sodium alginate, dioctyl sodium sulfosuccinate, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

55. The method according to claim 52, wherein the cationic surfactant is selected from the group consisting of quaternary ammonium compounds, benzalkonium chloride, cetyltrimethylammonium bromide, chitosans and lauryldimethylbenzylammonium chloride.

56. The method according to claim 52, wherein the surface active biological modifiers are selected from the group consisting of: albumin, casein, heparin, hirudin, or other proteins.

57. The method according to claim 51, wherein the pH adjusting agent is selected from the group consisting of: buffers, sodium hydroxide, hydrochloric acid, tris, citrate, acetate, lactate, meglumine and amino acids selected from the group consisting of glycine, alanine, leucine, isoleucine, lysine, methionine, tyrosine, phenylalanine, tryptophan, histidine, proline, serine, glutamic acid, aspartic acid, asparagine, glutamine, cysteine, and taurine.

58. The method according to claim 51, wherein the cyropreservation agent is selected from the group consisting of carbohydrates, glycerol, polyalkoxyethers, PEG-fatty acids and lipids, biologically-based surfactants, and other surface active agents.

59. The method according to claim 58, wherein the carbohydrate is selected from the group consisting of saccharides, disaccharides, and sugar alcohols.

60. The method according to claim 59, wherein the disaccharide is sucrose.

61. The method according to claim 59, wherein the sugar alcohol is mannitol.

62. The method according to claim 58, wherein the surface active agent is selected from the group consisting of polysorbates (Tweens), polyalkoxyethers, PEG-fatty acids, PEG-lipids, albumin, starch, glycerol, and dimethylsulfoxide.

63. The method according to claim 51, wherein the modulating agent is selected from the group consisting of carbohydrates, polymers, and proteins.

64. The method according to claim 51, wherein the excipient is present in an amount of about 0.001% to about 20% based on the total weight of the suspension.

65. The method according to claim 51, wherein the excipient is present in an amount of about 0.01% to about 5% based on the total weight of the suspension.

66. The method according to claim 50, wherein the volatile water immiscible solvent is selected from the group consisting of: linear, branched or cyclic alkanes with carbon number of 5 or higher, linear, branched or cyclic alkenes with carbon number of 5 or higher, linear, branched or cyclic alkynes with carbon number of 5 or higher; aromatic hydrocarbons completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents.

67. The method according to claim 50, wherein the volatile water immiscible solvent is methylene chloride.

68. The method according to claim 50, further comprises of the step of cooling the emulsion to about 4° C.

69. The method according to claim 50, wherein the step of mixing comprises the step of adding energy by a method selected from the group consisting of sonication, homogenization, microfluidization, counter current homogenization, and methods of providing impact, shear or cavitation forces, thermal input, either continuously or by temperature variation.

70. The method according to claim 50, wherein the step of removing the volatile water immiscible solvent is by sonicating.

71. The method according to claim 50, wherein the step of removing the volatile water immiscible solvent is by placing the microemulsion under a high vacuum.

72. The method according to claim 50, wherein the particles of the pharmaceutical agent are generally spherical in shape.

73. The method according to claim 29, wherein the solvent anti-solvent method comprises the steps of: dissolving the pharmaceutical agent in a water miscible solvent to form a non-aqueous solution; and combining the non-aqueous solution with an aqueous medium to precipitate the pharmaceutical agent to derive a pre-suspension.

74. The method according to claim 73, further comprising the step of agitating the pre-suspension to form a suspension.

75. The method according to claim 74, wherein the step of agitating comprises adding energy to the pre-suspension.

76. The method according to claim 75, wherein the energy-addition step comprises the step of importing energy to the pre-suspension using a method selected from the group consisting of sonication, homogenization, microfluidization, counter current homogenization, and methods of providing impact, shear or cavitation forces, or input of thermal energy, either continuously or by temperature variation.

77. The method according to claim 73, wherein the aqueous suspension further comprising one or more excipients selected from the group consisting of surface modifiers, pH adjusting agents, crystal growth modifiers, cryopreservation agents, osmotic agents, co-solvents, and viscosity modulating agent.

78. The method according to claim 77, wherein the surface modifier is selected from the group consisting of: anionic surfactants, cationic surfactants, nonionic surfactants and surface active biological modifiers.

79. The method according to claim 72, wherein the nonionic surfactant is selected from the group consisting of: polyoxyethylene fatty alcohol ethers, polyoxyethylene sorbitan fatty acid esters, polyoxyethylene fatty acid esters, polyoxyethylene-derivatized lipids such as Mpeg-PSPC (palmitoyl-stearoyl-phophatidylcholine), Mpeg-PSPE (palmitoyl-stearoyl-phophatidylethanolamine), sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

80. The method according to claim 78, wherein the anionic surfactant is selected from the group consisting of: potassium laurate, triethanolamine stearate, sodium lauryl sulfate, sodium dodecylsulfate, alkyl polyoxyethylene sulfates, sodium alginate, dioctyl sodium sulfosuccinate, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

81. The method according to claim 78, wherein the cationic surfactant is selected from the group consisting of quaternary ammonium compounds, benzalkonium chloride, cetyltrimethylammonium bromide, chitosans and lauryldimethylbenzylammonium chloride.

82. The method according to claim 78, wherein the surface active biological modifiers are selected from the group consisting of: albumin, casein, heparin, hirudin, or other proteins.

83. The method according to claim 77, wherein the pH adjusting agent is selected from the group consisting of: buffers, sodium hydroxide, hydrochloric acid, tris, citrate, acetate, lactate, meglumine and amino acids selected from the group consisting of glycine, alanine, leucine, isoleucine, lysine, methionine, tyrosine, phenylalanine, tryptophan, histidine, proline, seine, glutamic acid, aspartic acid, asparagine, glutamine, cysteine, and taurine.

84. The method according to claim 77, wherein the cyropreservation agent is selected from the group consisting of carbohydrates, glycerol, polyalkoxyethers, PEG-fatty acids and lipids, and biologically-based surfactants.

85. The method according to claim 84, wherein the carbohydrate is selected from the group consisting of saccharides, disaccharides, and sugar alcohols.

86. The method according to claim 85, wherein the disaccharide is sucrose.

87. The method according to claim 85, wherein the sugar alcohol is mannitol.

88. The method according to claim 84, wherein the surface active agent is selected from the group consisting of polysorbates (Tweens), polyalkoxyethers, PEG-fatty acids, PEG-lipids, albumin, starch, glycerol, and dimethylsulfoxide.

89. The method according to claim 76, wherein the viscosity modulating agent is selected from the group consisting of carbohydrates, polymers, and proteins.

90. The method according to claim 76, wherein the excipient is present in an amount of about 0.001% to about 20% based on the weight of the pre-suspension.

91. The method according to claim 76, wherein the excipient is present is an amount of about 0.01% to about 5% based on the weight of the pre-suspension.

* * * * *